United States Patent
Bilgic et al.

(10) Patent No.: US 9,542,763 B2
(45) Date of Patent: Jan. 10, 2017

(54) SYSTEMS AND METHODS FOR FAST RECONSTRUCTION FOR QUANTITATIVE SUSCEPTIBILITY MAPPING USING MAGNETIC RESONANCE IMAGING

(71) Applicants: Berkin Bilgic, Boston, MA (US); Kawin Setsompop, Charlestown, MA (US)

(72) Inventors: Berkin Bilgic, Boston, MA (US); Kawin Setsompop, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/693,525

(22) Filed: Apr. 22, 2015

(65) Prior Publication Data

US 2015/0310639 A1 Oct. 29, 2015

Related U.S. Application Data (60) Provisional application No. 61/984,501, filed on Apr. 25, 2014.

(51) Int. Cl.
*G06K 9/00* (2006.01)
*G06T 11/20* (2006.01)
(Continued)

(52) U.S. Cl.
CPC .......... *G06T 11/206* (2013.01); *A61B 5/4848* (2013.01); *G01R 33/243* (2013.01); *A61B 5/055* (2013.01);
(Continued)

(58) Field of Classification Search
CPC .................. G06T 11/206; A61B 5/4848
(Continued)

(56) References Cited

U.S. PATENT DOCUMENTS

| | | | |
|---|---|---|---|
| 8,886,283 B1 * | 11/2014 | Chen | 382/128 |
| 2011/0044524 A1 * | 2/2011 | Wang | G01R 33/54 382/131 |

OTHER PUBLICATIONS

Berkin Bilgic, Audrey P. Fan, Jonathan R. Polimeni, Stephen F. Cauley, Marta Bianciardi, Elfar Adalsteinsson, Lawrence L. Wald, and Kawin Setsompop, "Fast Quantitative Susceptibility Mapping with L1-Regularization and Automatic Parameter Selection", 2013, Wiley Periodicals Inc., Magnetic Resonance in Medicine 00:00-00 (2013), Retrieved from Internet on Apr. 27, 2016, retreived from URL: <http://martinos.org/~berkin/Bilgic_2013_Fast_QSM_MRM.pdf>.*

(Continued)

*Primary Examiner* — Gregory F Cunningham
(74) *Attorney, Agent, or Firm* — Quarles & Brady LLP (57) ABSTRACT

Described here are systems and methods for quantitative susceptibility mapping ("QSM") using magnetic resonance imaging ("MRI"). Susceptibility maps are reconstructed from phase images using an automatic regularization technique based in part on variable splitting. Two different regularization parameters are used, one, $\lambda$, that controls the smoothness of the final susceptibility map and one, $\mu$, that controls the convergence speed of the reconstruction. For instance, the regularization parameters can be determined using an L-curve heuristic to find the parameters that yield the maximum curvature on the L-curve. The $\mu$ parameter can be determined based on an $l_2$-regularization and the $\lambda$ parameter can be determined based on the iterative $l_1$-regularization used to reconstruct the susceptibility map.

14 Claims, 4 Drawing Sheets

(51) Int. Cl.
    *A61B 5/00*           (2006.01)
    *G01R 33/24*        (2006.01)
    *A61B 5/055*        (2006.01)
    *G01R 33/44*        (2006.01)
    *G01R 33/56*        (2006.01)
    *G01R 33/565*       (2006.01)

(52) U.S. Cl.
    CPC ............ *A61B 5/4082* (2013.01); *A61B 5/4088* (2013.01); *G01R 33/443* (2013.01); *G01R 33/5602* (2013.01); *G01R 33/56536* (2013.01)

(58) Field of Classification Search
    USPC ........................................................ 382/131
    See application file for complete search history.

(56) References Cited

OTHER PUBLICATIONS

Ludovic de Rochefort, Tian Liu, Bryan Kressler, Jing Liu, Pascal Spincemaille, Vincent Lebon, Jianlin Wu, and Yi Wang, "Quantitative Susceptibility Map Reconstruction from MR Phase Data Using Bayesian Regularization: Validation and Application to Brain Imaging", 2009, Wiley-Liss Inc., Magnetic Resonance in Medicine 63:194-206 (2010), Retrieved from Internet on Apr. 27, 2016, retrieved from URL: <http://onlinelibrary.wiley.com/doi/10.1002/mrm.22187/epdf>.*

* cited by examiner

SYSTEMS AND METHODS FOR FAST RECONSTRUCTION FOR QUANTITATIVE SUSCEPTIBILITY MAPPING USING MAGNETIC RESONANCE IMAGING

CROSS-REFERENCE TO RELATED APPLICATIONS

This application claims the benefit of U.S. Provisional Patent Application Ser. No. 61/984,501, filed on Apr. 25, 2014, and entitled "SYSTEMS AND METHODS FOR FAST RECONSTRUCTION FOR QUANTITATIVE SUSCEPTIBILITY MAPPING USING MAGNETIC RESONANCE IMAGING."

STATEMENT REGARDING FEDERALLY SPONSORED RESEARCH

This invention was made with government support under MH093765 and EB012107 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for fast reconstruction for quantitative susceptibility mapping ("QSM") using MRI.

Quantifying tissue iron concentration in vivo is important for understanding the role of iron in physiology and in neurological diseases associated with abnormal iron distribution. Excessive iron deposition in subcortical and brain stem nuclei occurs in a variety of degenerative neurological and psychiatric disorders including Alzheimer's disease, Huntington's Chorea, multiple sclerosis, and Parkinson's disease. Postmortem and in vivo studies have also revealed that deep gray matter brain structures accumulate iron at different rates throughout adult aging. Structures that exhibit iron accrual support components of cognitive and motor functioning. To the extent that excessive iron presence may attenuate neuronal function or disrupt connectivity, quantification and location of iron deposition may help explain age-related and disease-related motor slowing and other selective cognitive decline.

Several MRI techniques have been utilized for in vivo iron mapping and quantification. For example, one method capitalizes on the enhanced transverse relaxivity ($R_2$) of iron, by utilizing a field-dependent relaxation rate increase ("FDRI") approach, whereby $R_2$-weighted imaging is acquired at two different field strengths, attributing a relaxation enhancement at a higher field to iron. While FDRI relies on the modulation of signal intensity in MRI to infer iron concentration, MRI signal phase has also been proposed as a source signal for iron mapping, both by direct evaluation of phase images and reconstruction of magnetic susceptibility images from the phase data. Since local iron concentration is strongly correlated with the magnetic susceptibility, quantification of this paramagnetic property presents a sensitive estimate of iron concentration, although possibly complicated by more uncommon factors, such as pathological manganese deposition. Although phase mapping yields high-resolution, high-SNR data, estimating the underlying magnetic susceptibility suffers from non-local effects and spatial modulation artifacts due to the non-trivial mapping from susceptibility to phase.

Magnetic susceptibility, $\chi$, can be mapped to the observed phase shift in MRI via a well-understood transformation, yet the inverse problem, namely the estimation of $\chi$ from phase, is ill-posed due to zeros on a conical surface in the Fourier space of the forward transform. Hence, $\chi$ inversion benefits from additional regularization, which is an approach that commonly involves introducing additional information in order to solve an ill-posed problem or to prevent over-fitting.

Recently, regularization methods have been proposed for deriving susceptibility inversion. Specifically, smooth regions in the susceptibility map were promoted to match those of MR image magnitudes by introducing a weighted $l_2$-norm penalty on the spatial gradients of susceptibility, $\chi$. Likewise, another approach regularized the inversion by minimizing the $l_1$-norm of gradients of $\chi$, again weighted with a mask derived from MR image magnitudes. In addition, some proposed methods have used experimented $l_1$-norm and $l_2$-norm regularizations directly on the susceptibility values, rather than posing the minimization on the gradient coefficients.

Still another recent approach has been introduced to stabilize the susceptibility reconstruction problem by acquiring data at multiple orientations and inverting them simultaneously without regularization. Compared to regularized reconstruction techniques that employ a signal prior, such multi-orientation methods yield susceptibility maps with good quality, but at the cost of increased scan time and patient discomfort.

Therefore, given the above, there still remains a need for systems and methods for fast and accurate reconstruction of quantitative susceptibility maps.

SUMMARY OF THE INVENTION

The present invention overcomes the aforementioned drawbacks by providing a method for performing quantitative susceptibility mapping using a magnetic resonance imaging ("MRI") system. The method includes acquiring data, which may be susceptibility-weighted data, from a subject using the MRI system. Phase images are reconstructed from the acquired data, and at least one initial estimate of a susceptibility map is computed based on the reconstructed phase images. A first regularization parameter is determined based on the at least one initial estimate of the susceptibility map. A susceptibility map is then iteratively reconstructed using an $l_1$-minimization that comprises minimizing an objective function that includes the first regularization parameter and a second regularization parameter that is determined based on iterative updates of the susceptibility map.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for quantitative susceptibility mapping ("QSM") using magnetic resonance imaging ("MRI"). QSM aims to estimate the underlying magnetic susceptibility of the tissues that give rise to subtle changes in the magnetic field. Mapping this property allows quantification of tissue iron concentration and vessel oxygen saturation, and has found recent use in the investigation of neurodegenerative diseases, such as multiple sclerosis, and in the characterization of brain lesions.

Fast image reconstruction techniques for $l_1$ and $l_2$ regularized quantitative susceptibility mapping are provided. In some embodiments, the fast reconstruction techniques utilize an automatic regularization technique based in part on variable splitting. In these embodiments, the image reconstruction utilizes two different regularization parameters, λ and μ, one that controls the smoothness of the final image and one that controls the convergence speed of the reconstruction. For instance, using an L-curve heuristic, these parameters can be selected by finding the maximum curvature on the curve is selected as the optimal operating point. Sweeping the L-curve becomes practical with the proposed fast reconstruction, whereas parameter selection with Conjugate Gradient solver would take several hours of computation. More generally, the image reconstruction technique can employ regularization parameters that control the contribution of prior information into the final susceptibility map.

As one advantage, the systems and methods of the present invention can utilize an image reconstruction technique that can be adapted to include a constraint based on a magnitude prior without unduly increasing the overall reconstruction time.

The systems and methods of the present invention overcome the limitations of previous QSM approaches by utilizing regularized QSM algorithms for robust estimation of the magnetic susceptibility, χ, of tissues based on the phase, φ, of magnetic resonance data, such as gradient-recalled echo signals.

As another advantage, the systems and methods of the present invention can, based on the combination of fast phase unwrapping, background phase removal, regularization parameter estimation, and susceptibility inversion, provide reconstruction of large time-series datasets in a clinically reasonable time frame, thereby making investigation of functional BOLD QSM practical.

Given that magnetic susceptibility is a property of the underlying tissue, in some embodiments, the $l_1$-regularized QSM reconstruction can be based on the underlying assumption that susceptibility is approximately constant within regions of the same tissue type or within an anatomical structure. Based on this premise, the $l_1$-norm-penalized QSM algorithm can regularize the inversion by requiring the estimated χ to be sparse in the image gradient domain. On the other hand, placing an $l_2$-norm penalty on the spatial gradients of χ does not promote sparsity, but results in a large number of small gradient coefficients and, thus, incurs a smooth susceptibility reconstruction.

In addition to regularized susceptibility inversion, the systems and methods of the present invention can incorporate a background phase removal technique called SHARP (sophisticated harmonic artifact reduction for phase data) based on effective dipole fitting, which addresses the challenging problem of removing phase variations in the data that arise primarily from bulk susceptibility variations between air and tissue. SHARP filtering preserves the phase variations caused by internal susceptibility effects more faithfully than high-pass filtering, as employed in current implementations o susceptibility-weighted imaging ("SWI").

Tissue susceptibility χ is related to the measured field map φ via the relation, $$DF\chi = F\phi \qquad (1):$$

where F is the discrete Fourier Transform operator and, $$D = 1/3 - \kappa_z^2/\kappa^2 \qquad (2);$$

is the susceptibility kernel in k-space. This kernel effectively undersamples the frequency content of the field map on the conical surface, $$3\kappa_z^2 = k^2 \qquad (3);$$

which makes the inversion of the relation ill-conditioned. Existing approaches for performing this inversion improve its conditioning either by imposing prior knowledge on the reconstructed susceptibility map, or by collecting additional data by changing the orientation of the sample with respect to the main magnetic field.

Single-orientation, regularized QSM methods often impose sparsity or smoothness constraints on the spatial gradients of the reconstructed susceptibility map, which can be formulated by penalizing the $l_1$-norm or the $l_2$-norm of the gradients in three dimensions. The two types of regularized reconstruction methods can be expressed as an unconstrained convex optimization problem, minimizing either of the following:

$$\ell_1 - \text{regularized: } \frac{1}{2}\|F^{-1}DF\chi - \phi\|_2^2 + \alpha \cdot \|WG\chi\|_1; \qquad (4)$$

$$\ell_2 - \text{regularized: } \|F^{-1}DF\chi - \phi\|_2^2 + \beta \cdot \|WG\chi\|_2^2; \qquad (5)$$

where α and β are regularization parameters and $G=[G_x; G_y; G_z]$ is the gradient operator in three spatial dimensions. The diagonal weighting term, W, can either be taken to be the identity matrix, I, or a binary mask, $W=[W_x; W_y; W_z]$, that is derived from the magnitude signal. This binary mask can be employed to prevent penalizing certain gradient features.

These two optimization problems are conventionally solved with the iterative nonlinear Conjugate Gradient algorithm. Reconstruction times reported in the literature range between 20 minutes and 2-3 hours, which may be a limiting factor for the online reconstruction of susceptibility maps required for routine use or in clinical settings. Moreover, the parameters α and β need to be determined for optimal regularization, which is usually addressed by performing multiple reconstructions while sweeping a range of parameters to trace an L-curve, or by finding the operating point that satisfies a discrepancy principle. As such, identification of suitable amount of regularization would further increase the computation time.

A closed-form solution to the $l_2$-regularized QSM problem in Eqn. (5) without magnitude weighting (W=1) was recently proposed by B. Bilgic, et al., in "Regularized QSM in Seconds," *Proc. Intl. Soc Mag Reson. Med.* 21 (2013), Salt Lake City, USA.; p. 168. This method requires only two Fast Fourier Transform ("FFT") operations and takes less than a second to compute for a high-resolution phase data. In contrast, a closed-form solution to the $l_1$-constrained problem in Eqn. (4) does not exist, which forces the existing algorithms to operate iteratively.

Previously, $l_1$-regularized reconstruction was shown to be superior to $l_2$-penalty, both in image quality and quantification accuracy. The $l_1$-regularized results presented herein also show substantially reduced reconstruction error on numerical simulation, and better estimation of undersampled content near the magic angle on in vivo data. The systems and methods of the present invention utilize a fast $l_1$-regularized QSM algorithm that works iteratively; however, each iteration is computed efficiently in a closed-form. This fast $l_1$-regularized solver can be extended to incorporate a magnitude prior.

The systems and methods of the present invention utilize an efficient variable-splitting algorithm to solve Eqn. (4) without magnitude weighting, and provides up to a twentyfold speed-up in reconstruction time compared to the nonlinear Conjugate Gradient solver. By introducing an auxiliary variable that replaces the image gradient, each iteration of the proposed algorithm is computed in closed-form, requiring only Fast Fourier Transforms (FFTs) and soft thresholding operations.

With the proposed formulation, reconstruction for high-resolution in vivo susceptibility mapping at 0.6 mm isotropic voxel size can be accomplished in about one minute using a standard workstation. Combined with state-of-the-art phase unwrapping and background phase removal methods, this provides a fast reconstruction pipeline that might facilitate clinical application of QSM.

With the addition of a magnitude prior, the solution of both $l_1$-regularized and $l_2$-regularized problems become more involved because the related linear systems that need to be inverted are no longer diagonal. By employing a preconditioner that facilitates the inversion of these systems, a rapid iterative solver that leads to substantial computational savings can be obtained. Relative to the nonlinear CG method, the systems and methods of the present invention demonstrate a five-fold and fifteen-fold speed-up for the magnitude-weighted $l_1$-regularization and $l_2$-regularization, respectively.

In some embodiments, a fast algorithm for the reconstruction of undersampled k-space data in the context of compressed sensing is extended to susceptibility mapping without magnitude weighting (e.g., W=I) using the following formulation:

$$\min_{\chi,y} \frac{1}{2}\|F^{-1}DF\chi - \phi\|_2^2 + \lambda \cdot \|y\|_1 \text{ such that } G\chi = y. \quad (6)$$

This constrained optimization is first relaxed to an unconstrained optimization problem, then solved with a two-phase "split-Bregman" iteration: at iteration t, $$(\chi_{t+1}, y_{t+1}) = \operatorname*{argmin}_{\chi,y} \frac{1}{2}\|F^{-1}DF\chi - \phi\|_2^2 + \lambda \cdot \|y\|_1 + \frac{\mu}{2}\|y - G\chi - \eta_t\|_2^2; \quad (7)$$

$$\eta_{t+1} = \eta_t + G\chi_{t+1} - y_{t+1}. \quad (8)$$

Here, y is an auxiliary variable that replaces the gradient of the susceptibility map, $\chi$. By employing variable splitting, a closed-form optimization via a soft thresholding operator can be achieved. The variable, $\eta$, adds the mismatch in $G\chi=y$ back to the unconstrained problem to enforce this constraint. Eqn. (7) can be solved efficiently by iteratively minimizing with respect to $\chi$ and y separately:

$$\chi_{t+1} = \operatorname*{argmin}_\chi \left\{ \frac{1}{2}\|F^{-1}DF\chi - \phi\|_2^2 + \frac{\mu}{2}\|y_t - G\chi - \eta_t\|_2^2 \right\}; \quad (9)$$

$$y_{t+1} = \operatorname*{argmin}_y \left\{ \lambda \cdot \|y\|_1 + \frac{\mu}{2}\|y - G\chi_{t+1} - \eta_t\|_2^2 \right\}. \quad (10)$$

Eqn. (9) has a similar form to Eqn. (5) and can be solved in closed-form by taking the gradient and setting it to zero, $$(F^{-1}D^2F + \mu \cdot G^T G)\chi_{t+1} = F^{-1}DF\phi + \mu \cdot G^T(y_t - \eta_t) \quad (11).$$

Further simplification yields the update rule for $\chi$:

$$F\chi_{t+1} = (D^2 + \mu \cdot (E_x^2 + E_y^2 + E_z^2))^{-1} \cdot (DF\phi + \mu \cdot E^H F(y_t - \eta_t)) \quad (12).$$

Here, $E^H = [E_x^H, E_y^H, E_z^H]$ and the variables $y_t$ and $\eta_t$ have components in three dimensions, $y_t = [y_{t,x}; y_{t,y}; y_{t,z}]$ and $\eta_t = [\eta_{t,x}; \eta_{t,y}; \eta_{t,z}]$. The matrix inversion involves only diagonal matrices and needs to be computed once. The cost of evaluating Eqn. (12) is three FFT operations (one for each spatial axis) and element-wise multiplications. The update for the susceptibility map is performed in k-space, thereby avoiding one redundant inverse FFT operation per iteration.

Solution to the $l_1$-regularized least squares problem in Eqn. (10) is given by the element-wise soft thresholding operation, $$y_{t+1} = \max\left(|G\chi_{t+1} - \eta_t| - \frac{\lambda}{\mu}, 0\right) \cdot \operatorname{sign}(G\chi_{t+1} + \eta_t). \quad (13)$$

This operator is applied to all three components of $y_{t+1}$. To compute the gradient in x-direction, $G_x\chi_{t+1}$, the k-space representation of the current susceptibility estimate, $F\chi_{t+1}$, is utilized due to $G_x\chi_{t+1} = F^{-1}E_x(F\chi_{t+1})$. This way, the update rule in Eqn. (13) requires three inverse FFT operations (one for each spatial axis) and simple thresholding operations.

Combining Eqns. (8), (12), and (13) together yields the complete algorithm for the proposed $l_1$-regularized reconstruction:

TABLE 1

Proposed Variable - Splitting Algorithm for $l_1$-Regularized QSM

| | |
|---|---|
| initialization: | $y_{0,x} = y_{0,y} = y_{0,z} = \eta_{0,x} = \eta_{0,y} = \eta_{0,z} = 0$ |
| update: | $F\chi_{t+1} = (D^2 + \mu \cdot (E_x^2 + E_y^2 + E_z^2))^{-1} \times$ $(DF\phi + \mu(E_x^H F(y_{t,x} - \eta_{t,x}) + E_y^H F(y_{t,y} - \eta_{t,y}) + E_z^H F(y_{t,z} - \eta_{t,z})))$ |
| gradient update: | $\begin{cases} G_x\chi_{t+1} = F^{-1}E_x(F\chi_{t+1}) \\ G_y\chi_{t+1} = F^{-1}E_y(F\chi_{t+1}) \\ G_z\chi_{t+1} = F^{-1}E_z(F\chi_{t+1}) \end{cases}$ |

TABLE 1-continued

Proposed Variable - Splitting Algorithm for $l_1$-Regularized QSM soft thresh-olding:
$$\begin{cases} y_{t+1,x} = \max(|G_x\chi_{t+1} + \eta_{t,x}| - \lambda/\mu, 0) \cdot \text{sign}(G_x\chi_{t+1} + \eta_{t,x}) \\ y_{t+1,y} = \max(|G_y\chi_{t+1} + \eta_{t,y}| - \lambda/\mu, 0) \cdot \text{sign}(G_y\chi_{t+1} + \eta_{t,y}) \\ y_{t+1,z} = \max(|G_z\chi_{t+1} + \eta_{t,z}| - \lambda/\mu, 0) \cdot \text{sign}(G_z\chi_{t+1} + \eta_{t,z}) \end{cases}$$

residual update:
$$\begin{cases} \eta_{t+1,x} = \eta_{t,x} + G_x\chi_{t+1} - y_{t+1,x} \\ \eta_{t+1,y} = \eta_{t,y} + G_y\chi_{t+1} - y_{t+1,y} \\ \eta_{t+1,z} = \eta_{t,z} + G_z\chi_{t+1} - y_{t+1,z} \end{cases}$$

Per iteration, the proposed method requires six FFT operations (three for $F\chi$ update and another three for gradient update) and simple thresholding operations.

In some embodiments, the proposed method introduces a second regularization parameter, $\mu$, that can be determined. This parameter does not change the solution to the optimization problem, but affects the convergence speed. Empirically, a parameter that leads to fast convergence can be identified on one subject, which might then generalize to different datasets. Alternatively, an automatic parameter selection can be implemented, as will now be described.

At the first iteration of the proposed algorithm, the initial estimate of the susceptibility map can be selected using the initial condition $y_0=\eta_0=0$ in Eqn. (12). This yields, $$F\chi_1 = (D^2 + \mu \cdot (E_x^2 + E_y^2 + E_z^2))^{-1} \cdot DF\phi \quad (14).$$

This expression is the same that gives an optimizer for an $l_2$-regularized QSM formulation. As a result, the first iteration of the proposed $l_1$-constrained algorithm can be computed as the solution to the original $l_2$-regularized problem in Eqn. (5). Based on this, the regularization parameter, $\mu$, can be selected as the optimal value of $\beta$ found for the closed-form $l_2$-reconstruction. The algorithm terminates when the change in k-space of the susceptibility falls below a threshold, such as one percent.

To hasten convergence, a nonlinear Conjugate Gradient algorithm can use the closed-form $l_2$-reconstruction as initial guess, and the termination criterion can again be selected as less than one percent change in susceptibility.

The regularization parameter, $\mu$, controlling the gradient consistency term $\mu \cdot \|y - G\chi - \eta_t\|_2^2$ in the variable-splitting algorithm does not affect the solution, but instead affects the speed of convergence.

Figure 1A:
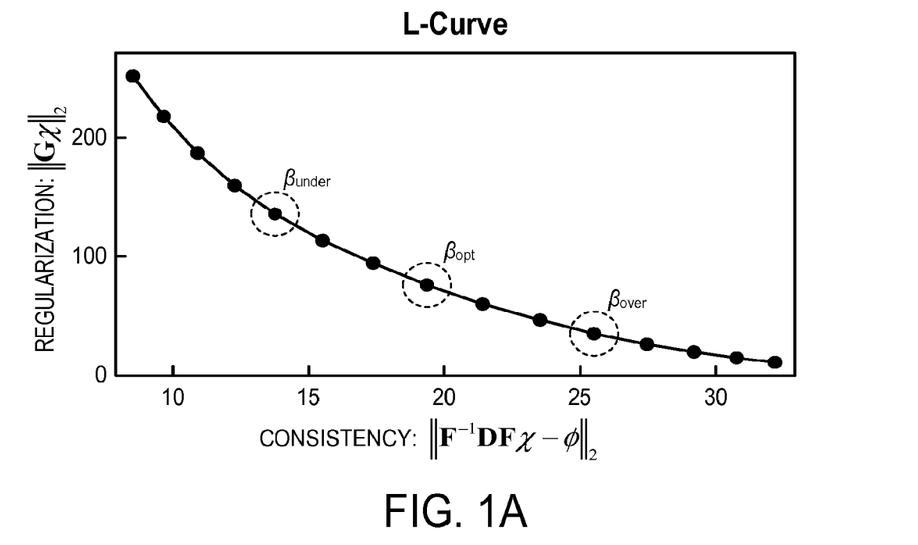
FIGS. 1A and 1B illustrate examples of L-curve and curvature of L-curve plots based on an $l_2$-reconstruction, which are used to determine a first regularization parameter, $\beta = \mu$, in accordance with some embodiments of the present invention.
Figure 1B:
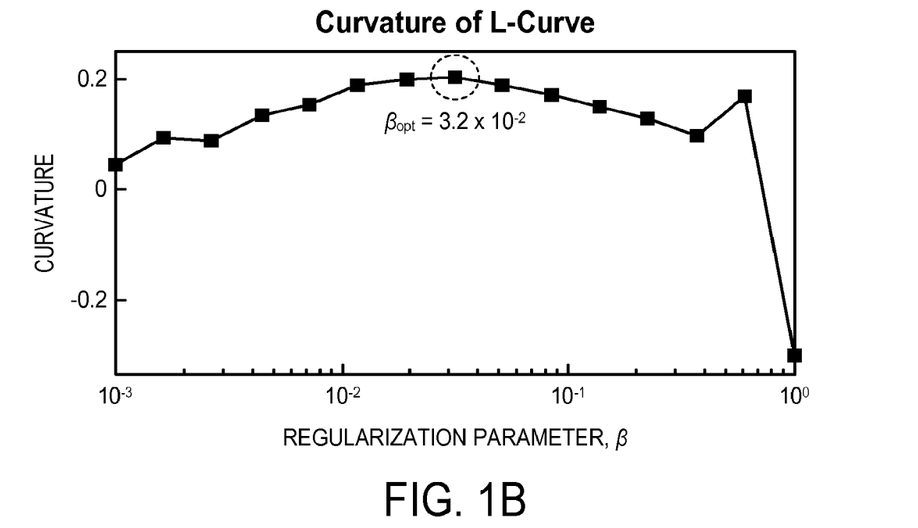

The regularization parameter $\beta$ for the closed-form $l_2$-regularization without magnitude prior was selected using the L-curve heuristic (FIGS. 1A and 1B). When the L-curve traced by the data consistency and regularization terms as $\beta$ varied does not have a clear elbow point, as it does not in FIG. 1A, the point with the largest curvature can be selected as the optimal operating point, as indicated in FIG. 1B. The curvature, $\kappa$, was computed as, $$\kappa = 2\frac{\ddot{\rho}\dot{\omega} - \ddot{\omega}\dot{\rho}}{(\dot{\rho}^2 + \dot{\omega}^2)^{1.5}}; \quad (15)$$

where $$\rho = \log(\|F^{-1}DF\chi - \phi\|_2^2) \quad (16);$$

$$\omega = \log(\|G\chi\|_2^2) \quad (17);$$

and where $\dot{\omega}$, $\dot{\rho}$, $\ddot{\omega}$ and $\ddot{\rho}$ represent first and second derivatives of $\omega$ and $\rho$ with respect to $\beta$. Because the L-curve is only sampled at discrete points, cubic splines can be fit to $\rho$ and $\omega$ to express them as smooth functions of $\beta$, which can then be differentiated.

In the example illustrated in FIGS. 1A and 1B, tracing the L-curve with the $l_2$-based method took 42 seconds, where 15 reconstructions were made for logarithmically-spaced $\beta$ values between $10^{-3}$ and 1. The setting that maximized the curvature of the L-curve was found to be $\beta=3.2\times10^2$, which was taken to be the optimal smoothing parameter value. Two additional reconstructions with under-regularization and over-regularization are depicted in FIG. 1A for comparison. Computation time for each $l_2$-based susceptibility map was 0.9 seconds.

By way of example, a fast solution to the closed-form $l_2$-reconstruction, without magnitude weighting can be provided as follows. The global optimizer of the convex optimization problem in Eqn. (5) can be obtained by taking the gradient and setting it to zero, $$F^{-1}D^2F + \beta \cdot G^TG)\chi = F^{-1}DF\phi \quad (18).$$

The solution of this linear system is facilitated by evaluating the spatial gradient via multiplication in k-space rather than using convolution in image space. This can be accomplished by expressing the image gradient along the x-axis as $G_x = F^{-1}E_xF$, where $E_x$ is a diagonal matrix that provides the k-space representation of the image-domain differencing operator, $\delta_x - \delta_{x-1}$. $E_x$ can be constructed by starting from the vector $v_x$ with entries, $$v_x(i) = 1 - \exp(-2\pi\sqrt{-1} \cdot i/N_x), \quad (19);$$

where $i = 0, \ldots, N_x - 1$ and $N_x$ is the matrix size along x. When $v_x$ replicated along $k_y$ and $k_z$ dimensions in k-space to generate an image volume of size $N_x \times N_y \times N_z$, the matrix $E_x$ can be obtained by assigning this volume to diagonal entries of $E_x$. The operators $E_y$ and $E_z$ are similarly defined. Eqn. (18) then becomes, $$(F^{-1}D^2F + \beta \cdot F^{-1}(E_x^2 + E_y^2 + E_z^2))\chi = F^{-1}DF\phi \quad (20).$$

Further simplification yields, $$\chi = F^{-1} \cdot (D^2 + \beta(E_x^2 + E_y^2 + E_z^2))^{-1} \cdot DF\phi \quad (21).$$

Note that the matrix inversion now involves only diagonal matrices; hence, it is straightforward to evaluate. The total cost of this $l_2$-regularized QSM is then two FFT operations and summation and multiplication of diagonal matrices. These usually take less than a second for three-dimensional high-resolution image volume and thus is acceptable for computing the regularization parameter, $\mu$, in the $l_1$-regularized QSM method.

Figure 2A:
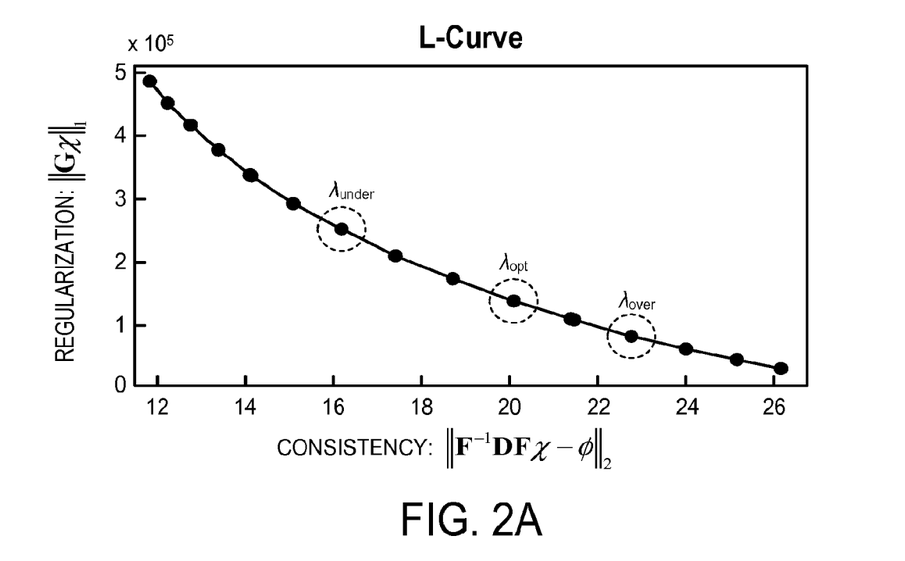
FIGS. 2A and 2B illustrate examples of L-curve and curvature of L-curve plots based on an $l_1$-reconstruction, which are used to determine a second regularization parameter, λ, in accordance with some embodiments of the present invention.
Figure 2B:
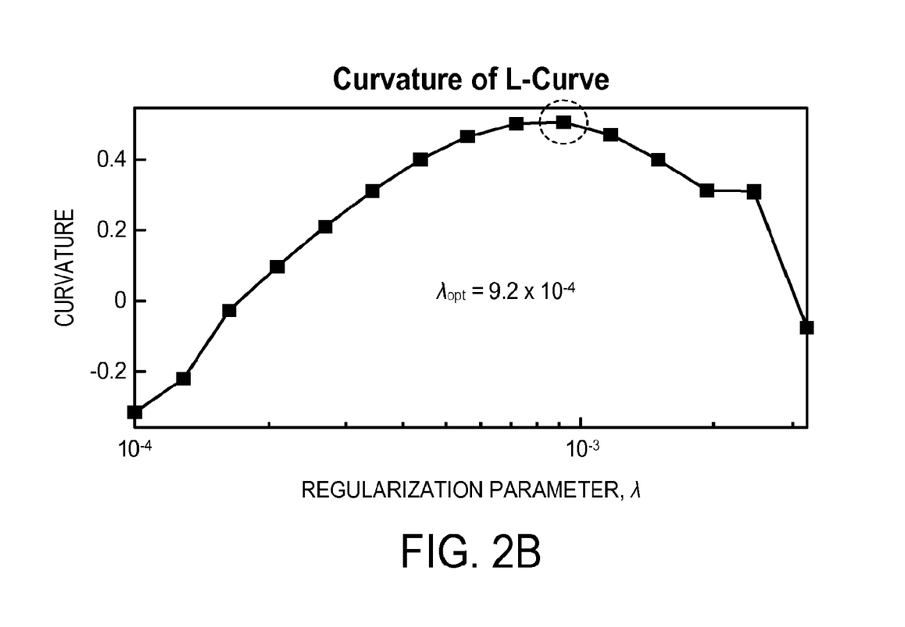

Regarding the proposed $l_1$-based method without magnitude weighting, the smoothing parameter, $\lambda$, can similarly be determined by maximizing the curvature of the L-curve (FIGS. 2A and 2B). Each point on the L-curve in the example in FIG. 2A was reconstructed using ten iterations of the proposed algorithm. Based on the observation that the initial iteration yields the $l_2$-regularized reconstruction, the consistency parameter, $\mu$, was set to the optimal $\beta$ determined for the closed-form solution. The algorithm terminated when there was less than one percent change in the k-space of the susceptibility map.

The smoothing parameter value corresponding to the largest curvature on the L-curve for the proposed $l_1$-regularization was found to be $\lambda = 9.2 \cdot 10^{-4}$ in the example illustrated in FIGS. 2A and 2B. Total reconstruction time in this example for 15 reconstructions with logarithmically-spaced $\lambda$ values between $10^{-4}$ and $10^{-2.5}$ was 710 seconds. Under-regularized, optimally-regularized, and over-regularized susceptibility maps are plotted in FIG. 2A. Processing time for the optimally-smoothed reconstruction was 60 seconds and convergence criterion was met in 13 iterations.

The reconstruction described above can be extended to include a magnitude prior constraint. Edge priors, W, derived from a magnitude image can be encoded in the variable-splitting framework by solving, $$\min_{\chi,y}\left\{\frac{1}{2}\|F^{-1}DF\chi - \phi\|_2^2 + \lambda \cdot \|y\|_1\right\} \text{ such that } WG\chi = y. \quad (22)$$

While the update rules in the preceding section remain largely the same, solution of the interim linear system in Eqn. (11) becomes more involved, $$(F^{-1}D^2F + \mu \cdot G^T W^T G)\chi_{t+1} = DF\phi + \mu \cdot G^T W^T (y_t - \eta_t) \quad (23).$$

Further simplification leads to the following system, $$(D^2 + \mu \cdot E^H F W^2 F^{-1} E) F\chi_{t+1} = DF\phi + \mu \cdot E^H F W^T (y_t - \eta_t) \quad (24).$$

Eqn. (24) can be efficiently solved with a linear conjugate gradient method by employing the preconditioner $(D^2 + \mu \cdot E^2)$, which is diagonal and thus its inverse is straightforward to compute, thereby making it convenient to use it as a preconditioner. Convergence behavior can be substantially enhanced if the solution from the previous iteration, $\chi_t$, is used as an initial guess. As the variable-splitting algorithm iterates, the difference between the successive solutions, $\chi_t$ and $\chi_{t+1}$, decrease progressively. Using such a suitable initial guess, the preconditioned conjugate gradient can solve Eqn. (24) within one percent tolerance in a small number of steps.

Reconstruction with $l_1$-regularization using magnitude prior employed the same $\mu$ and $\lambda$ parameters identified from the L-curve analysis described above. The tolerance of the preconditioned conjugate gradient used at each iteration was set to one percent, and the algorithm terminated when the updates between iterations was below one percent.

When using the magnitude-weighted $l_1$-regularized QSM method, the regularization parameter, $\mu$, is preferably determined using an L-curve analysis based on a magnitude-weighted $l_2$-reconstruction. With the inclusion of magnitude weighting, W, the system that needs to be solved becomes, $$(F^{-1}D^2F + G^T W^2)\chi = F^{-1}DF\phi \quad (25).$$

Expressing the gradients in k-space and simplification leads to, $$(D^2 + \beta \cdot E^H F W^2 F^{-1} E) F\chi = DF\phi \quad (26);$$

where $E = [E_x; E_y; E_z]$. Because this system is no longer diagonal, its inversion is more involved. The linear conjugate gradient algorithm is a popular technique used for solution of such symmetric, positive definite systems. The convergence speed of this method is determined by the condition number of the matrix, $$A = (D^2 + \beta \cdot E^H F W^2 F^{-1} E) \quad (27).$$

The conditioning can be improved if the matrix, A, can be brought closer to being identity I. The closed-form solution can be used as preconditioner, which allows solving the modified system, $$(D^2 + \beta \cdot E^2)^{-1} \cdot \{A \cdot F\chi - DF\phi\} = 0 \quad (28).$$

As mentioned above, because $(D^2 + \beta \cdot E^2)$ is diagonal, it is straightforward to compute its inverse and convenient to use it as a preconditioner. As an example, when the gradients of the magnitude image are thresholded so that the strongest thirty percent of voxels within a tissue mask are considered to be edges, the resulting W matrix is equal to the identity matrix, I, except for about five percent of its entries. This makes the approximation $(D^2 + \beta \cdot E^2)^{-1} \approx A^{-1}$ valid, and renders the preconditioner useful. The closed-form solution can be used as an initial guess to further accelerate convergence.

As one example, the proposed magnitude-weighted $l_2$-based reconstruction with the preconditioned conjugate gradient solver can use the same $\beta$ parameter as described above. In this an other examples, the termination criterion for this iterative approach can be selected as attaining 0.1 percent tolerance, where tolerance is defined $\|A\chi - b\|_2 / \|b\|_2$ regarding the solution of the system $A\chi = b$. As an example, the magnitude prior can be derived by thresholding the spatial gradients of the magnitude signal so that a certain percentage, such as thirty percent, of voxels in a tissue mask with the strongest gradients are considered to be edges.

In some embodiments, the smoothing parameter, $\alpha$, for the $l_1$-regularized nonlinear Conjugate Gradient method can be selected so that the data consistency of the final susceptibility map, $\|F^{-1}DF\chi - \phi\|_2^2$, matches the consistency of the proposed reconstruction. This strategy aims to obtain comparable amounts of regularization with the two $l_1$-penalized algorithms.

Figure 3:
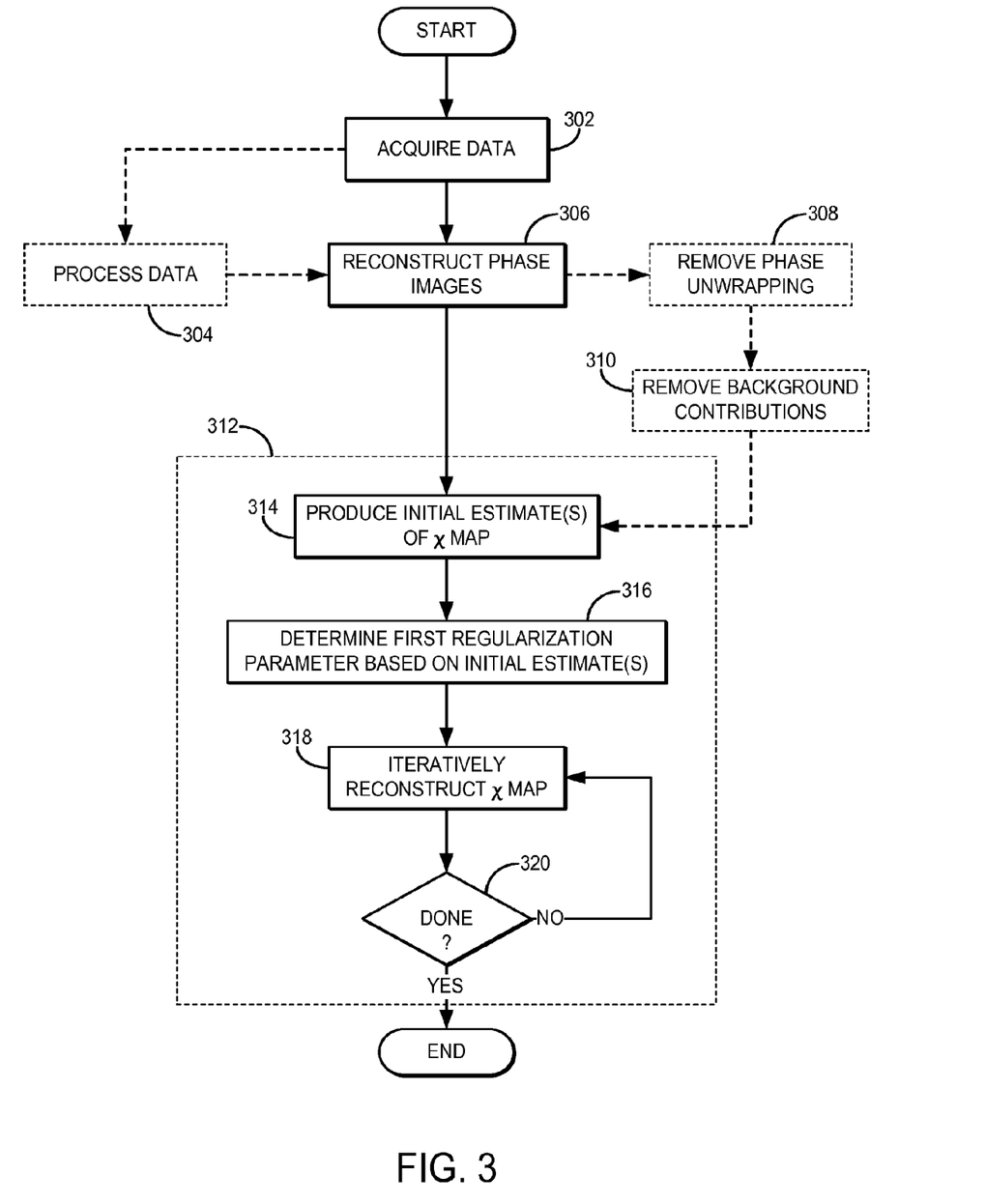
FIG. 3 is a flowchart setting forth the steps of an example of a method for quantitative susceptibility mapping using a fast $l_1$-regularized quantitative susceptibility mapping ("QSM") reconstruction.

Referring now to FIG. 3, a flowchart setting forth the steps of an example method for reconstructing quantitative susceptibility maps from data acquired with a magnetic resonance imaging ("MRI") system is illustrated. The method includes acquiring data with the MRI system, as indicated at step 302. As an example, data can be acquired as susceptibility-weighted data or other data containing suitable phase information.

The acquired data can optionally be processed, as indicated at step 304. As one example of optional processing, a relative phase offset can be estimated and removed from the acquired data. For instance, the relative phase offset can be estimated from a center subgroup of pixels (e.g., the center 3×3×3 pixels) and removed from each coil. In another example, the radio frequency ("RF") phase offset of each channel at TE=0 can be estimated using a linear fit to the phase images corresponding to the acquired echoes. The estimated offset per channel can then removed from the phase data.

The acquired data, whether additionally processed or not, is then reconstructed to form phase images, as indicated at step 306. Optionally, a magnitude-weighted, phase-valued coil combination can be performed, which is given by, $$\psi_{combo} = \measuredangle\left(\sum_i m_i \cdot \exp(\sqrt{-1} \cdot \psi_i)\right). \quad (29)$$

The combined phase images can be masked using a binary-valued region-of-interest ("ROI"), which in some embodiments can be generated using the FSL brain extraction tool ("BET") described by F. Smith in "Fast robust automated brain extraction," *Human brain mapping*, 2002; 17:143-155. As an example, this mask can be based on the first frame in the time series oh phase images.

Phase unwrapping can be applied to the phase images, as indicated at step 308. As an example, phase unwrapping can be performed with a fast Laplacian unwrapping algorithm. Background contributions due to air-tissue interfaces can also be removed, as indicated at step 310. For instance, these contributions can be removed with SHARP filtering.

Reconstruction of quantitative susceptibility maps is then performed on the phase images, as generally indicated at 312. In general, the reconstruction includes producing an initial estimate of the quantitative susceptibility map, as indicated at step 314. In some embodiments, the initial estimate of the quantitative susceptibility map is computed using the closed-form $l_2$-regularized QSM algorithm described above. In some other embodiments, the initial estimate of the quantitative susceptibility map is computed using the magnitude prior constrained closed-form $l_2$-regularized QSM algorithm described above. Based on the initial estimate, a first regularization parameter, μ, is determined, as indicated at step 316. As an example, the regularization parameter μ can be selected with the L-curve analysis technique described above using a mean tissue phase averaged over a select number of image frames as the input. For instance, the select number of image frames can be the first thirty image frames in an image series. The gradient consistency parameter, μ, for the $l_1$-based method is set to the β value determined by L-curve.

Using the initial estimate and the first regularization parameter, μ, an updated quantitative susceptibility map is iteratively reconstructed, as indicated at step 318. In some embodiments, the $l_1$-based reconstruction without magnitude prior described above is used to reconstruct the updated quantitative susceptibility map. This reconstruction utilizes two regularization parameters: μ and λ. The second regularization parameter, λ, can be selected with the L-curve analysis technique described above using a mean tissue phase averaged over a select number of image frames as the input. For instance, the select number of image frames can be the first thirty image frames in an image series. In some other embodiments, the magnitude prior constrained $l_1$-based reconstruction described above can be used.

The reconstruction of the quantitative susceptibility maps concludes when a stopping criterion is satisfied, as indicated at decision block 320. As an example, the stopping criterion can be when satisfied when there is less than a one percent signal change in quantitative susceptibility maps generated in successive iterations.

Thus, systems and methods for fast quantitative susceptibility mapping based on an $l_1$-regularized reconstruction have been provided. The systems and methods of the present invention are capable of achieving a twenty-fold processing speed-up relative to conventional nonlinear conjugate gradient solvers. Compared to the previously reported computation times (20 minutes to several hours), the systems and methods of the present invention drastically reduce the processing time for a whole brain, high-resolution dataset down to one minute. These efficient formulations of $l_1$-regularized quantitative susceptibility mapping are therefore capable of facilitating the clinical use of susceptibility mapping.

Combined with the previously Laplacian phase unwrapping and SHARP filtering, the systems and methods of the present invention provide a fast processing pipeline that produces susceptibility maps from wrapped phase data. As each dipole inversion can be completed rapidly, automatic estimation of the regularization parameter also becomes practical. The systems and methods of the present invention are capable of tracing the L-curve faster than the time it would take a conjugate gradient solver to complete a single reconstruction.

For in vivo whole brain susceptibility mapping at 0.6 mm isotropic resolution, the complete pipeline of phase processing, parameter estimation and $l_1$-regularized QSM takes under fourteen minutes. As the optimal smoothing parameters would be expected to remain within a certain range across different datasets, it is contemplated that the parameter estimation time can be further reduced by considering a smaller interval of values. For studies that involve scanning multiple subjects with similar imaging parameters, it might also be possible to determine the regularization amount on one subject, and apply this to the rest of the subjects in the study.

The variable-splitting approach described here offers two advantages over previous variable-splitting techniques applied to quantitative susceptibility mapping. First, the method described here introduces only one auxiliary variable, y. Other techniques have included a second auxiliary variable that penalizes tissue phase, φ. This second auxiliary variable requires the introduction of a third regularization parameter. Because the tissue phase, φ, is the observed data, however, it is not necessary to penalize these observations. The variable-splitting approach described here is thus more compact and efficient than previous attempts.

Second, the method described here extends the variable-splitting algorithm to admit magnitude weighting on the spatial gradients. Magnitude-weighted regularization aims to avoid smoothing across strong edges identified on the magnitude signal. Because the linear system involved in the magnitude-weighted reconstruction is no longer diagonal, the method described here utilizes a preconditioned conjugate gradient solver for rapid matrix inversion. Despite the increased complexity of the optimization problem, the resulting $l_1$-regularized algorithm with magnitude prior is still five times faster than the nonlinear CG technique. Herein, $l_2$-regularized QSM is also extended to admit prior information derived from the magnitude signal. While the resulting optimization problem is no longer solved in closed-form, the proposed preconditioned linear solver allows significant computational savings.

Although the smoothing parameters β and λ were selected with the L-curve method, the amount of regularization can also be tailored to a particular problem while using the L-curve parameter values as useful landmarks (e.g., a parameter that is ten percent less than the L-curve selected value can be employed for reduced smoothing). Once the regularization parameter is selected on a single time point, the same value can be applied to the rest of the volumes in the time-series. This point constitutes a significant computational difference between the high-resolution 3D GRE dataset and the functional QSM experiment.

To compensate for the noise variation in the field map, a diagonal weighting, M, proportional to the image magnitude can be included in the data consistency term. With this refinement, the $l_2$-constrained problem becomes, $$\min_{\xi} \|M(F^{-1}DF\chi - \phi)\|_2^2 + \beta \cdot \|WG\chi\|_2^2. \tag{30}$$

The optimizer of this expression is given by the solution of, $$(D^TFM^2F^{-1}D + \beta \cdot E^HFW^2F^{-1}E)F\chi = D^TFM^2F^{-1}DF\phi \tag{31};$$

This system is preferably solved iteratively, and the preconditioner $(D^2+\beta \cdot E^2)$ is expected to be less effective compared to its use without the additional noise weighting, M. A similar system arises in the update formula for $l_1$-based reconstruction, $$(D^TFM^2F^{-1}D + \mu E^TFW^2F^{-1}E)F\chi_{t+1} = D^TFM^2F^{-1}DF\phi + \mu E^TFW^T(y_t - \eta_t) \tag{32}.$$

It is contemplated that employing efficient matrix factorization algorithms will facilitate these more challenging matrix inversion problems.

Figure 4:
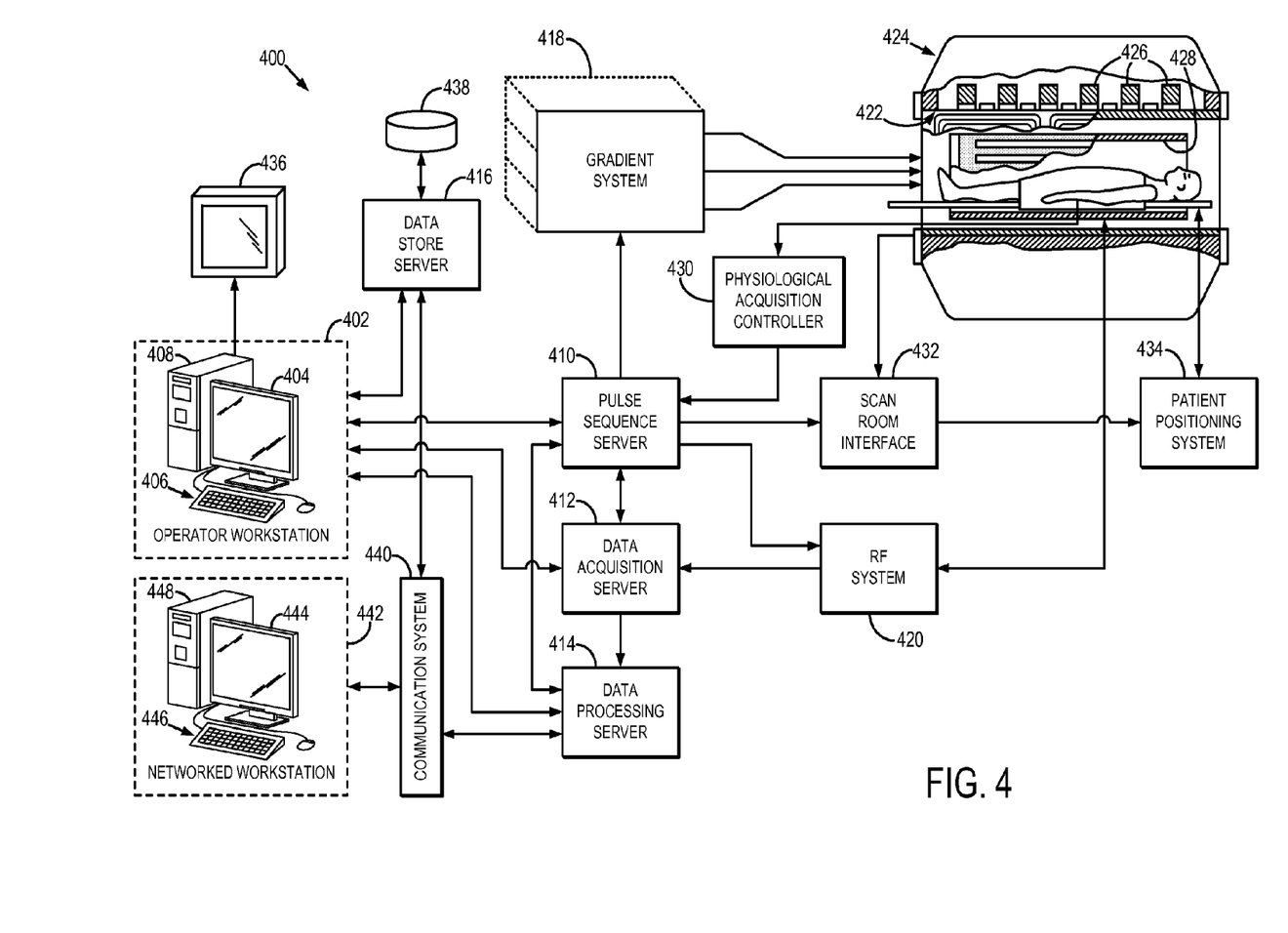
FIG. 4 is a block diagram of an example of a magnetic resonance imaging ("MRI") system.

Referring particularly now to FIG. 4, an example of a magnetic resonance imaging ("MRI") system 400 is illustrated. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil (not shown in FIG. 4), in order to perform the prescribed magnetic resonance pulse sequence. Responsive magnetic resonance signals detected by the RF coil 428, or a separate local coil (not shown in FIG. 4), are received by the RF system 420, where they are amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil arrays (not shown in FIG. 4).

The RF system 420 also includes one or more RF receiver channels. Each RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \tag{33}$$

and the phase of the received magnetic resonance signal may also be determined according to the following relationship:

$$\varphi = \tan^{-1}\left(\frac{Q}{I}\right). \tag{34}$$

The pulse sequence server 410 also optionally receives patient data from a physiological acquisition controller 430. By way of example, the physiological acquisition controller 430 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to detect the arrival of a contrast agent in a magnetic resonance angiography ("MRA") scan. By way of example, the data acquisition server 412 acquires magnetic resonance data and processes it in real-time to produce information that is used to control the scan.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may exchanged between the data processing server 414 or the data store server 416 and the networked workstations 442, such that the data or images may be remotely processed by a networked workstation 442. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for performing quantitative susceptibility mapping using a magnetic resonance imaging (MRI) system, the steps of the method comprising:
   a) acquiring data from a subject using the MRI system;
   b) reconstructing phase images from the acquired data;
   c) computing at least one initial estimate of a susceptibility map based on the reconstructed phase images;
   d) determining a first regularization parameter based on the at least one initial estimate of the susceptibility map; and
   e) reconstructing a susceptibility map using an $l_1$-minimization that comprises iteratively minimizing an objective function that includes the first regularization parameter and a second regularization parameter, wherein the second regularization parameter is undated in each iteration based on iterative updates to the susceptibility map in that iteration.

2. The method as recited in claim 1, wherein the objective function introduces an auxiliary variable that replaces an image gradient term, such that the $l_1$-minimization has a closed form.

3. The method as recited in claim 1, wherein step c) includes computing the at least one initial estimate of the susceptibility map using an $l_2$-minimization that comprises minimizing an objective function that includes the first regularization parameter.

4. The method as recited in claim 3, wherein the objective function in the $l_2$-minimization includes a magnitude prior.

5. The method as recited in claim 3, wherein the first regularization parameter is determined in step d) based on an L-curve computed using a consistency condition enforced in the $l_2$-minimization and a regularization used in the $l_2$-minimization.

6. The method as recited in claim 5, wherein the first regularization parameter is determined in step d) based on a curvature of the L-curve.

7. The method as recited in claim 6, wherein the first regularization parameter is determined in step d) as a point of maximum curvature in the curvature of the L-curve.

8. The method as recited in claim 1, wherein step e) includes determining the second regularization parameter based on an L-curve computed using a consistency condition enforced in the $l_1$-minimization and a regularization used in the $l_1$-minimization.

9. The method as recited in claim 8, wherein the second regularization parameter is determined in step e) based on a curvature of the L-curve.

10. The method as recited in claim 9, wherein the second regularization parameter is determined in step e) as a point of maximum curvature in the curvature of the L-curve.

11. The method as recited in claim 1, wherein step b) further comprises processing the reconstructed phase images to remove phase wrapping.

12. The method as recited in claim 1, wherein step b) further comprises removing a relative phase offset from the acquired data before reconstructing the phase images.

13. The method as recited in claim 1, wherein the objective function in the $l_1$-minimization includes a magnitude prior.

14. The method as recited in claim 1, wherein the data acquired in step a) is susceptibility-weighted data.

* * * * *

UNITED STATES PATENT AND TRADEMARK OFFICE
CERTIFICATE OF CORRECTION

PATENT NO. : 9,542,763 B2
APPLICATION NO. : 14/693525
DATED : January 10, 2017
INVENTOR(S) : Bilgic et al.

It is certified that error appears in the above-identified patent and that said Letters Patent is hereby corrected as shown below:

In the Specification

Column 6, Line 27, Equation (12),

"$F\chi_{t+1} = \left(D^2 + \mu \cdot (E_x^2 + E_y^2 + E_z^2)\right)^{-1} \sim \left(DF\phi + \mu \cdot E^H F(y_t - \eta_t)\right)$"

should be -- $F\chi_{t+1} = \left(D^2 + \mu \cdot (E_x^2 + E_y^2 + E_z^2)\right)^{-1} \cdot \left(DF\phi + \mu \cdot E^H F(y_t - \eta_t)\right)$ --.

Column 9, Line 44, Equation (25), "$(F^{-1}D^2 F + G^T W^2 G)\chi = F^{-1} DF\phi$"

should be -- $(F^{-1}D^2 F + \beta \cdot G^T W^2 G)\chi = F^{-1} DF\phi$ --.

In the Claims

Column 16, Line 2, Claim 1, "undated" should be --updated--.

Signed and Sealed this
Twenty-eighth Day of March, 2017

Michelle K. Lee
*Director of the United States Patent and Trademark Office*